US008884052B2

(12) United States Patent
Duff et al.

(10) Patent No.: US 8,884,052 B2
(45) Date of Patent: Nov. 11, 2014

(54) PRODUCTION OF DIACETOXYETHYLENE BY DIRECT ACETOXYLATION

(75) Inventors: Joseph G. Duff, League City, TX (US); Stephen Kerlegon, League City, TX (US); Kien V. Phung, Pearland, TX (US); Daniel Rangel-Osalde, League City, TX (US); Tatiana H. Sonnenberg, Houston, TX (US); Cathy L. Tway, Shepherd, MI (US); Hang Wang, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 46 days.

(21) Appl. No.: 13/327,401

(22) Filed: Dec. 15, 2011

(65) Prior Publication Data
US 2013/0158289 A1 Jun. 20, 2013

(51) Int. Cl.
*C07C 67/035* (2006.01)

(52) U.S. Cl.
USPC .......................................... 560/261

(58) Field of Classification Search
USPC .......................................... 560/261
See application file for complete search history.

(56) References Cited

U.S. PATENT DOCUMENTS

| | | |
|---|---|---|
| 5,001,259 A | 3/1991 | Smith et al. |
| 5,185,308 A | 2/1993 | Bartley et al. |
| 5,691,267 A | 11/1997 | Nicolau et al. |
| 6,040,474 A | 3/2000 | Jobson et al. |
| 6,114,571 A | 9/2000 | Abel et al. |
| 6,180,821 B1 | 1/2001 | Jobson et al. |
| 6,228,226 B1 * | 5/2001 | Hess et al. ............... 203/53 |
| 6,476,261 B2 | 11/2002 | Ellis et al. |
| 6,603,038 B1 | 8/2003 | Hagemeyer et al. |
| 6,696,596 B1 | 2/2004 | Herzog et al. |
| 6,852,877 B1 | 2/2005 | Zeyss et al. |
| 2012/0149939 A1 | 6/2012 | Kotsianis et al. |

FOREIGN PATENT DOCUMENTS

| | | |
|---|---|---|
| EP | 0330853 A2 | 9/1989 |
| EP | 0672453 A2 | 9/1995 |
| FR | 1361270 A | 5/1964 |
| GB | 1271104 A | 4/1972 |
| GB | 1559540 A | 1/1980 |
| WO | WO 97/38790 A1 | 10/1997 |

OTHER PUBLICATIONS

International Search Report and Written Opinion mailed Apr. 11, 2013 in corresponding International Application PCT/US2012/068896.
Masahiro Yamaji et al., "Catalytic Diacetoxylation of Dihaloethylenes in the Presence of Palladium Salts", Bulletin of the Chemical Society of Japan, 1973, pp. 90-93, vol. 46, No. 1.

* cited by examiner

*Primary Examiner* — Yong Chu
*Assistant Examiner* — Sonya Wright

(57) ABSTRACT

In one embodiment, the invention is to a process for producing a vinyl acetate composition by contacting a vinyl acetate stream with acetic acid, ethylene, and oxygen to form a reaction mixture and reacting the reaction mixture in a reactor under conditions effective to form a crude vinyl acetate composition comprising vinyl acetate, water, acetic acid and at least 0.1 wt % diacetoxyethylene.

12 Claims, 2 Drawing Sheets

PRODUCTION OF DIACETOXYETHYLENE BY DIRECT ACETOXYLATION

FIELD OF THE INVENTION

This invention relates to processes for producing a vinyl acetate composition and, in particular, to improved processes for producing a vinyl acetate composition comprising vinyl acetate and valuable by-products.

BACKGROUND OF THE INVENTION

Vinyl acetate is an important monomer in the production of polyvinyl acetate and polyvinyl alcohol products. Vinyl acetate is conventionally prepared by contacting acetic acid and ethylene with molecular oxygen to form a crude vinyl acetate composition. The reaction is typically conducted in the presence of a suitable catalyst, which may comprise palladium, an alkali metal acetate promoter, and, optionally, a co-promoter, e.g., gold or cadmium, on a catalyst support. U.S. Pat. No. 6,696,596, for example, indicates that it is well known to manufacture vinyl acetate in a reaction in the gas phase with acetic acid and oxygen or oxygen containing gasses over fixed-bed catalysts. U.S. Pat. No. 6,040,474, as another example, describes the manufacture of acetic acid and/or vinyl acetate using two reaction zones wherein the first reaction zone comprises ethylene and/or ethane for oxidation to acetic acid and the second reaction zone comprises acetic acid and ethylene with the product streams being subsequently separated thereby producing vinyl acetate. Also, U.S. Pat. No. 6,476,261, describes an oxidation process for the production of alkenes and carboxylic acids such as ethylene and acetic acid, which are reacted to form vinyl acetate, demonstrating that more than one reaction zone can be used to form the vinyl acetate.

This vinyl acetate reaction, however, lends itself to the production of several by-products including, for example, non-volatile residues such as polymerized vinyl acetate, polymerized ethylene, and heavy ends, such as acetoxyacetic acid and others. Conventionally, the formation of these by-products has been deemed to be detrimental in many respects. For example, the formation of these by-products 1) reduces vinyl acetate yield and 2) may lead to fouling of vinyl acetate production equipment, e.g., purification towers and vaporizers. In conventional processes, a heavy ends tower is utilized to remove these by-products, which are then discarded or incinerated.

In some cases, however, some of these by-products may have value. As such, the formation and improved separation thereof may be beneficial.

Thus, the need exists for improved processes for producing vinyl acetate compositions that 1) yield higher amounts of potentially valuable by-products and/or 2) better facilitate the overall vinyl acetate separation scheme.

The disclosures of all of the references mentioned above are hereby incorporated by reference.

SUMMARY OF THE INVENTION

The present invention, in one embodiment, is to a method for producing a vinyl acetate composition. The process comprising the steps of (a) contacting a vinyl acetate stream with acetic acid, ethylene, and oxygen to form a reaction mixture, and (b) reacting the reaction mixture in a reactor under conditions effective to form a crude vinyl acetate composition comprising vinyl acetate, water, acetic acid and at least 0.1 wt % diacetoxyethylene.

In another embodiment, the invention is to a vinyl acetate composition. The vinyl acetate composition comprises vinyl acetate and at least 0.1 wt % diacetoxyethylene.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
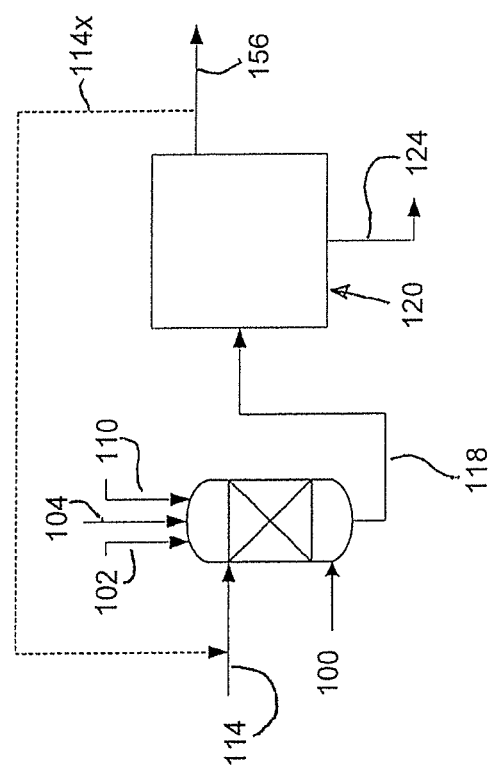
FIG. 1 is a schematic diagram of a portion of a vinyl acetate production process, illustrating an embodiment that provides for increased production of diacetoxyethylenes.

Conventional vinyl acetate production processes yield vinyl acetate compositions that comprise not only vinyl acetate, but many unwanted by-products such as non-volatile residues and heavy ends. The formation of these by-products reduces yield and has detrimental effects on production equipment. Examples of affected production equipment include purification towers and vaporizers. As a result, typical vinyl acetate processes seek to minimize or eliminate the formation of these by-products. Further, significant resources typically are devoted to separation of these by-products from the crude vinyl acetate composition and to the subsequent disposal thereof.

It has now been discovered, however, that some of these by-products, in particular diacetoxyethylenes, e.g., cis- and trans-diacetoxyethylenes, may be commercially valuable, if successfully separated and collected. For example, the diacetoxyethylenes may have the following structural formulae:

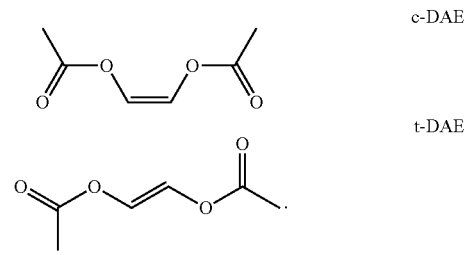

Accordingly, the present invention relates to the increase of diacetoxyethylene concentrations in vinyl acetate compositions. It has been found that the addition of vinyl acetate, e.g., vinyl acetate monomer (VAM), directly or indirectly, to a vinyl acetate reactor results in a crude vinyl acetate composition, e.g., a reactor effluent stream, comprising higher amounts of diacetoxyethylenes. The additional vinyl acetate may be fresh vinyl acetate and/or vinyl acetate that is recycled from other point in the process. Thus, in one embodiment, the invention is to a process for producing a vinyl acetate composition comprising the step of contacting a vinyl acetate stream with acetic acid, ethylene, and oxygen (pure or in a mixture, e.g., air), to form a reaction mixture. The additional vinyl acetate may be added to at least one of the reactant feed streams and/or directly into a vinyl acetate reactor. Preferably, the vinyl acetate is added upstream of the reactor.

The inventive process further comprises the step of reacting the reaction mixture under conditions effective to form a crude vinyl acetate composition comprising vinyl acetate and at least 0.1 wt % diacetoxyethylene. The crude vinyl acetate composition may also comprise water and acetic acid, e.g., residual acetic acid. Of course, vinyl acetate is formed as a reaction product and this vinyl acetate may be present in the reactor. The present invention contacts additional vinyl acetate, e.g., vinyl acetate other than the product vinyl acetate, with the reactants and products in the reactor to promote diacetoxyethylene formation. The addition of a separate vinyl acetate stream to the conventional reactants, e.g., acetic acid, ethylene, and oxygen, provides for a crude vinyl acetate composition that, as formed, comprises increased amounts of diacetoxyethylene, as compared to the crude vinyl acetate compositions prepared from conventional methods that do not add an additional vinyl acetate stream to the reaction mixture. As one benefit, more diacetoxyethylene is formed, which can then be utilized and/or sold. As one example, the diacetoxyethylene may be used as monomeric reactants to produce polymers.

Heavy ends from conventional vinyl acetate formation processes may include ethylene glycol, ethylidene diacetate, ethylene glycol monoacetate, vinyl acetoxy acetate, ethylene glycol diacetate, cis-diacetoxyethylene, trans-diacetoxyethylene, glycolic acid, acetoxyacetic acid, and mixtures thereof. As noted above, however, these by-products are generally considered to be undesired and the formation thereof is typically minimized.

As a result of the inventive process, the crude vinyl acetate composition comprises vinyl acetate and an increased concentration of diacetoxyethylenes. In one embodiment, the crude vinyl acetate composition comprises at least 0.1 wt % diacetoxyethylenes, e.g., at least 0.2 wt %, or at least 0.3 wt %, or at least 0.4 wt %, or at least 0.5 wt %, or even at least 1 wt %. In terms of ranges, the crude vinyl acetate composition may comprise diacetoxyethylenes in amounts ranging from about 0.1 wt % to 1.0 wt %, e.g., from 0.2 wt % to 0.5 wt %, or from 0.3 wt % to 0.4 wt %.

In one embodiment, the diacetoxyethylene in the crude vinyl acetate composition comprises an isomeric mixture comprising cis-diacetoxyethylene, trans-diacetoxyethylene, and optionally 1,1-diacetoxyethylene. The weight ratio of cis-diacetoxyethylene to trans-diacetoxyethylene in the crude reaction effluent composition is typically about 1:3, or 1:2, or even 1:1.

In a preferred embodiment, the diacetoxyethylene in the crude vinyl acetate composition comprises at least 0.1 wt % cis-diacetoxyethylene and trans-diacetoxyethylene, combined, e.g., at least 0.3 wt % or at least 0.5 wt %. Accordingly, when the combined amount of cis- and trans-diacetoxyethylene is 0.1 wt %, the amount of cis-diacetoxyethylene is about 0.025 wt % and the amount of trans-diacetoxyethylene is about 0.075 wt %; and when the combined amount of cis- and trans-diacetoxyethylene is 0.3 wt %, the amount of cis-diacetoxyethylene is about 0.075 wt % and the amount of trans-diacetoxyethylene is about 0.225 wt %; and when the combined amount of cis- and trans-diacetoxyethylene is 0.5 wt %, the amount of cis-diacetoxyethylene is about 0.125 wt % and the amount of trans-diacetoxyethylene is about 0.375 wt %.

The crude vinyl acetate composition may be further processed to separate the components thereof. In one embodiment, the inventive process further comprises the step of separating the crude vinyl acetate composition to form a purified vinyl acetate stream and at least one by-product stream. The purified vinyl acetate stream comprises vinyl acetate and reduced amounts of by-products, as compared to the crude vinyl acetate composition. At least one of the by-product streams comprises at least a portion of the diacetoxyethylene that was initially present in the crude product stream. In one embodiment, as a result of the additional vinyl acetate to the reaction mixture, the by-product stream(s) comprise higher amounts of diacetoxyethylene, e.g., at least 4.6 wt % diacetoxyethylene, at least 5 wt % or at least 10 wt %. In terms of ranges, the by-product stream(s) may comprise from 4.6 wt % to 16 wt % diacetoxyethylene. e.g., from 5 wt % to 15 wt %.

Advantageously, the separated diacetoxyethylene can be recovered for other uses. In one embodiment, the by-product stream comprises at least 1% of the diacetoxyethylene that was initially present in the crude vinyl acetate stream, e.g., at least 5% or at least 10%. When higher amounts of diacetoxyethylene are present in the crude vinyl acetate mixture, separation efficiencies are improved and higher amounts of the diacetoxyethylene are separated and recovered.

Any suitable separation techniques may be employed to perform the separation. Examples include single or multiple distillations of the crude effluent stream, sometimes followed by adsorption techniques, precipitation techniques, or crystallization techniques, depending on the purity of diacetoxyethylenes desired. An exemplary separation scheme is shown in FIG. 1.

In a preferred embodiment, at least a portion of the purified vinyl acetate stream is recycled to the reactor, e.g., to provide the additional vinyl acetate to the reaction mixture. In other embodiments, fresh vinyl acetate, e.g., vinyl acetate from an outside source, may be added to the reactor to provide the additional vinyl acetate to the reaction mixture. In other embodiments, both fresh and recycled vinyl acetate are added to the reactor. As noted above, the crude vinyl acetate composition, as formed, comprises vinyl acetate, (residual) acetic acid, (residual) oxygen, water, and, optionally, residual ethylene and an initial amount of by-products, e.g., NVR, heavy ends (including diacetoxyethylenes), peroxides, and/or mixtures thereof. In one embodiment, the crude vinyl acetate composition comprises one or more by-products. In one embodiment, the crude vinyl acetate composition comprises at least 5 wt. % vinyl acetate, e.g., at least 10 wt. %, at least 15 wt. %, or at least 20 wt. %; and at least 10 wppm impurities, e.g., at least 100 wppm, at least 500 wppm, at least 1,000 wppm, or at least 2,000 wppm. In terms of ranges, the crude vinyl acetate composition optionally comprises from 1 wt. % to 75 wt. % vinyl acetate, e.g., from 1 wt. % to 50 wt. %, from 2 wt. % to 35 wt. %, or from 5 wt. % to 15 wt. %; and from 10 wppm to 15,000 wppm impurities, e.g., from 100 wppm to 10,000 wppm, or from 500 wppm to 5,000 wppm. In terms of upper limits, the crude vinyl acetate composition optionally comprises less than 15,000 wppm impurities, e.g., less than 10,000 or less than 5,000.

In copending U.S. Provisional Application No. 61/407, 684, filed Oct. 28, 2010, incorporated herein in its entirety, a process for inhibiting formation of impurities is disclosed. In this process, a crude vinyl acetate effluent stream from a vinyl acetate reaction process is contacted with one or more scavengers. The use of the scavenger(s) is thought to reduce peroxide formation, thus avoiding the formation of oxygen radicals, which can initiate or catalyze the undesirable formation of polymers of ethylene and/or vinyl acetate. Exemplary scavengers include ascorbic acid, thiols, polyphenols, hydroquinone, 4-hydroxy-TEMPO, methyl hydroquinone, 2,2-biphenol, 4,4'-dihydroxybiphenol, 2,5-di-tert-butylhydroquinone, 2,6-di-tert-butyl-4-methylphenol, 4-methoxyphenol, (butylated) hydroxyanisole, nitrosobenzene, resorcinol, tert-butyl hydroquinone, tert-butylhydroquinone, 2-tert-butyl-4-methylphenol, 1,2,4-benzenetriol, N,N'-di-2-butyl-1,4-phenylenediamine, 2,4-dimethyl-6-tert-butylphenol, 2,6-di-tertbutylphenol, substituted alkylamines, parabenzoquinone, butylated hydroxytoluene, diphenyl picryl hydrazyl, and mixtures thereof.

In contrast, in one embodiment of the present invention, incorporation of and contact with such scavengers is reduced or avoided altogether. In one embodiment, the concentration of scavengers utilized in the inventive process is limited to be less than about 10 wppm, or even less than 1 wppm, based on the weight of the crude vinyl acetate effluent stream.

Vinyl Acetate Formation

Conventionally, formation of vinyl acetate may be carried out by reacting acetic acid and ethylene in the presence of oxygen. In other embodiments, the features of the present invention may apply to production of other monomers such as, for example, vinyl esters, or diacetoxyethylene. This reaction may take place heterogeneously with the reactants being present in the gas phase. The reactor may be configured such that the reactor is capable of removing heat from the reaction. Suitable reactor types include, but are not limited to, a fixed bed reactor and a fluidized bed reactor. Preferably, the molar ratio of ethylene to acetic acid in the reaction ranges from 1:1 to 10:1, e.g., from 1:1 to 5:1; or from 2:1 to 3:1. In one embodiment, the molar ratio of ethylene to oxygen in the reaction ranges from 1:1 to 20:1, e.g., from 1.5:1 to 10:1; or from 2:1 to 5:1. In another embodiment, the molar ratio of acetic acid to oxygen in the reaction ranges from 1:1 to 10:1, e.g., from 1:1 to 5:1; or from 1:1 to 3:1.

The acetic acid may be produced by any suitable method. As one example, the acetic acid may be produced via methanol carbonylation with carbon monoxide. Water may be formed in situ in a liquid reaction composition, for example, by the esterification reaction between the methanol reactant and the acetic acid product. In one embodiment, water is introduced to the carbonylation reactor together with or separately from other components of the liquid reaction composition. Water may be separated from other components of reaction composition, withdrawn from the reactor, and may be recycled in controlled amounts to maintain the required concentration of water in the liquid reaction composition. Preferably, the concentration of water maintained in the liquid reaction composition is in the range of from 0.1 wt. % to 16 wt. %, e.g., from 1 wt. % to 14 wt. %, or from 1 wt. % to 10 wt. %.

In another embodiment, the carbonylation reaction is a low water carbonylation, wherein the concentration of water maintained in the liquid reaction composition ranges from 0.1 wt. % to 14 wt. %, e.g., from 1 wt. % to 10 wt. %. The low water carbonylation may be conducted by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The disclosure of U.S. Pat. No. 5,001,259 is hereby incorporated by reference. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The ethylene similarly may be produced by any suitable method. In one embodiment, the ethylene is formed via the hydrogenation of acetic acid followed by the dehydration of the acetic acid to form ethylene. As another alternative, the acetic acid and the ethylene may be produced via oxidation of an alkane, e.g., ethane, as discussed in U.S. Pat. No. 6,476,261, the disclosure of which is hereby incorporated by reference. The oxygen used in the formation of vinyl acetate in the method of the present invention may further comprise other inert gases such as nitrogen. As one example, the oxygen used in the vinyl acetate reaction is provided by an air stream.

In one embodiment, additional ethylene may be fed to the reactor. This additional ethylene, as well as the reactant ethylene mentioned above, may be substantially pure. In one embodiment, the ethylene may be admixed, for example, with one or more of nitrogen, methane, carbon dioxide, carbon monoxide, hydrogen, and low levels of $C_3/C_4$ alkenes/alkanes. Additional oxygen may be fed to the reactor. The additional oxygen, if used, may be air or a gas richer or poorer in molecular oxygen than air. One suitable additional molecular oxygen-containing gas may be, oxygen diluted with a suitable diluent, for example nitrogen or carbon dioxide. Preferably, the additional molecular oxygen-containing gas is oxygen. Preferably, at least some of the oxygen is fed to the reactor independently from the ethylene and acetic acid.

The vinyl acetate reaction may suitably be carried out at a temperature in the range of from 100° C. to 300° C., e.g., from 140° C. to 220° C. or from 150° C. to 200° C. In another embodiment, the reaction may be carried out pressure in the range of from 0.1 MPa to 10 MPa, e.g., from 0.1 MPa to 2.5 MPa or from 1 MPa to 2.5 MPa.

Preferably, the reaction is conducted over a catalyst. Suitable catalysts include catalysts comprising a first metal and optionally one or more of a second metal, a third metal, or additional metals. The catalyst optionally comprises a catalyst support. The first and optional second and third metals may be selected from palladium, gold, boron, alkali metals, and Group IB or VIIIB transition metals.

The first metal optionally is present in an amount from 0.1 to 10 wt. %, e.g., from 0.2 to 5 wt. %, or from 0.2 to 2.5 wt. %. The additional metals, if present, may be present in amounts ranging from 0.1 to 10 wt. %, e.g., from 0.2 to 5 wt. %, or from 0.2 to 2.5 wt. %. In other embodiments, the catalyst may comprise metalloids, e.g., boron, in amounts ranging from 0.01 wt. % to 1 wt. %, e.g., from 0.01 wt. % to 0.2 wt. %. For catalysts comprising two or more metals, the two or more metals may be alloyed with one another. Alternatively, the two or more metals may comprise a non-alloyed metal solution or mixture. Also, the preferred metal ratios may vary depending on the metals used in the catalyst. If palladium and gold are utilized, the ratio may range from 0.5:1 to 20:1, e.g., from 1.8:1 to 10:1. In some exemplary embodiments where a first and second metal are used, the mole ratio of the first metal to the second metal is from 5:1 to 1:1, e.g., from 3:1 to 1:1, or from 2:1 to 1:1.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, from 1 wt. % to 8 wt. %, from 1 wt. % to 5 wt. %, or from 2 wt. % to 4 wt. %, based on the total weight of the catalyst.

Suitable support materials may include silica, alumina, silica-alumina, titania, ticano-silicates, zirconia, zircono-silicate, niobia, silicates, alumino-silicates, titanates, carbon, metals, and glasses. Preferred supports include zirconia, zircono-silicates, and titano-silicates. Suitable support modifiers may include barium, magnesium, cerium, potassium, calcium, niobium, tantalum, titanium, yttrium, strontium, zirconium, vanadium, molybdenum, and rubidium. Preferred support modifiers include niobium, titanium, magnesium, and zirconium.

Specific examples of suitable catalysts include, for example, those described in GB 1 559 540; EP 0 330 853; EP 0 672 453; U.S. Pat. Nos. 5,185,308; 5,691,267; 6,114,571; 6,852,877; and 6,603,038. The disclosures of all of the above-mentioned references are hereby incorporated by reference.

GB 1 559 540 describes suitable catalysts that can be employed in the preparation of vinyl acetate by the reaction of ethylene, acetic acid and oxygen. The catalysts are comprised of: (1) a catalyst support having a particle diameter of from 3 to 7 mm and a pore volume of from about 0.2 to 1.5 ml per gram, a 10% by weight water suspension of the catalyst support having a pH from about 3.0 to 9.0, (2) a palladium-gold alloy distributed in a surface layer of the catalyst support, the surface layer extending less than 0.5 mm from the surface of the support, the palladium in the alloy being present in an amount of from about 1.5 to 5.0 grams per liter of catalyst, and the gold being present in an amount of from about 0.5 to 2.25 grams per liter of catalyst, and (3) from 5 to 60 grams per liter of catalyst of alkali metal acetate.

U.S. Pat. No. 5,185,308 describes a shell impregnated catalyst active for the production of vinyl acetate from ethylene, acetic acid, and an oxygen-containing gas, the catalyst consisting essentially of (1) a catalyst support having a particle diameter from about 3 to about 7 mm and a pore volume of 0.2 to 1.5 ml per gram, (2) palladium and gold distributed in the outermost 1.0 mm thick layer of the catalyst support particles, and (3) from about 3.5 to about 9.5% by weight of potassium acetate wherein the gold to palladium weight ratio in said catalyst is in the range 0.6 to 1.25.

U.S. Pat. No. 5,691,267 describes a two step gold addition method for a catalyst used in the gas phase formation of vinyl acetate from the reaction of ethylene, oxygen, and acetic acid. The catalyst is formed by (1) impregnating a catalyst carrier with aqueous solutions of a water-soluble palladium salt and a first amount of a water-soluble gold compound such as sodium-palladium chloride and auric chloride, (2) fixing the precious metals on the carrier by precipitating the water-insoluble palladium and gold compounds by treatment of the impregnated carriers with a reactive basic solution such as aqueous sodium hydroxide which reacts with the palladium and gold compounds to form hydroxides of palladium and gold on the carrier surface, (3) washing with water to remove the chloride ion (or other anion), and (4) reducing all the precious metal hydroxides to free palladium and gold, wherein the improvement comprises (5) impregnating the carrier with a second amount of a water-soluble gold compound subsequent to fixing a first amount of water-soluble gold agent, and (6) fixing the second amount of a water-soluble gold compound.

U.S. Pat. No. 6,114,571 describes a catalyst for forming vinyl acetate in the gas phase from ethylene, acetic acid, and oxygen or oxygen-containing gases wherein the catalyst is comprised of palladium, gold, boron, and alkali metal compounds on a support. The catalyst is prepared by a) impregnating the support with soluble palladium and gold compounds; b) converting the soluble palladium and gold compounds on the support into insoluble compounds by means of an alkaline solution; c) reducing the insoluble palladium and gold compounds on the support by means of a reducing agent in the liquid phase; d) washing and subsequently drying the support; e) impregnating the support with a soluble alkali metal compound; and f) finally drying the support at a maximum of 1500° C., wherein boron or boron compounds are applied to the catalyst prior to the final drying.

U.S. Pat. No. 6,603,038 describes a method for producing catalysts containing metal nanoparticles on a porous support, especially for gas phase oxidation of ethylene and acetic acid to form vinyl acetate. The invention relates to a method for producing a catalyst containing one or several metals from the group of metals comprising the sub-groups Ib and VIIIb of the periodic table on porous support particles, characterized by a first step in which one or several precursors from the group of compounds of metals from sub-groups Ib and VIIIb of the periodic table is or are applied to a porous support, and a second step in which the porous, preferably nanoporous support to which at least one precursor has been applied is treated with at least one reduction agent, to obtain the metal nanoparticles produced in situ in the pores of said support.

EP 0 672 453 describes palladium-containing catalysts and their preparation for fluid bed vinyl acetate processes.

An advantage of using a palladium-containing catalyst is that any carbon monoxide produced in a prior reaction zone will be consumed in the presence of oxygen and the palladium-containing catalyst in the second reaction zone. An example of a prior reaction zone is a reaction zone for preparing the reactants. This eliminates the need for a separate carbon monoxide removal reactor.

The vinyl acetate reaction may be characterized in terms of conversions based on the reactants. In one embodiment, acetic acid conversions range from 1% to 100%, e.g., from 5% to 50% or from 10% to 45%. Oxygen conversions may range from 1% to 100%, e.g., from 20% to 100% or from 20% to 50%. Ethylene conversions may range from 1% to 90%, e.g., from 5% to 100% or from 10% to 50%. However, conversion of ethylene into diacetoxyethylenes or other by-products should be limited to be less than 5%, preferably less than 1%. That is, the process is advantageously conducted such that ethylene conversion into vinyl acetate is not diminished, as compared to a conventional vinyl acetate production process. In one embodiment, vinyl acetate selectivity, based on ethylene may range from 20% to 100%, e.g., from 50% to 95% or from 75% to 90%.

In conventional processes, higher product yields, e.g., vinyl acetate yields and/or higher diacetoxyethylene yields, could, in theory, be achieved by increasing ethylene and/or acetic acid conversions. Increasing these conversions, however, would inevitably reduce the amount of oxygen available for diacetoxyethylene production. Advantageously, the addition of vinyl acetate to the reaction, in accordance with the present invention, provides for higher overall vinyl acetate and/or diacetoxyethylene yields without increasing ethylene and/or acetic acid conversions. In one embodiment, the vinyl acetate formation reaction has an ethylene conversion less than 5% and the crude vinyl acetate composition comprises diacetoxyethylene in the inventive amounts.

In the vinyl acetate reaction, the catalyst may have a productivity (measured in space time yield, STY) ranging from 10 g/hr-liter to 5,000 g/hr-liter, e.g., from 100 g/hr-liter to 2,000 g/hr-liter or from 200 g/hr-liter to 1,000 g/hr-liter, where g/hr-liter means grams of vinyl acetate per hour per liter of catalyst. In terms of upper limits, the space time yield maybe less than 20,000 g/hr-liter, e.g., less than 10,000 g/hr-liter or less than 5,000 g/hr-liter.

FIG. 1 illustrates an exemplary vinyl acetate production process in accordance with the present invention. The process of FIG. 1 shows reactor 100 and separation zone 120. Oxygen feed 102 provides an oxygen-containing gas, e.g., a pure oxygen stream or an air stream, to reactor 100. Ethylene feed 104 provides ethylene to reactor 100. Acetic acid feed 110 provides acetic acid to reactor 100. In preferred embodiments, vinyl acetate feed 114 provides vinyl acetate, e.g., vinyl acetate monomer, to reactor 100. The vinyl acetate in vinyl acetate feed 114 may, in some embodiments, be fresh vinyl acetate. Although FIG. 1 shows vinyl acetate feed 114 as a separate feed line, in other embodiments, the vinyl acetate feed may be combined with oxygen feed 102, ethylene feed 104, and/or acetic acid feed 110 in any combination. Some additional exemplary locations for vinyl acetate feed streams are discussed below.

Reactor 100 reacts acetic acid, vinyl acetate, and ethylene in the presence of oxygen to form the crude vinyl acetate product. The crude vinyl acetate composition exits the reactor via line 118 and is directed to separation zone 120. Separation zone 120 separates the crude vinyl acetate composition into at least one by-product stream 124 and a purified vinyl acetate stream 156. The by-stream product comprises by-products, e.g., diacetoxyethylene, and the purified vinyl acetate comprises vinyl acetate and a reduced amount, if any, by-products. By-product stream(s) 124 may be further separated to recover the components thereof, e.g., diacetoxyethylene. Purified vinyl acetate stream may be further processed and/or commercialized, e.g., sold or utilized in other processes such as a polyvinyl alcohol production process. Because purified vinyl acetate stream 156 comprises vinyl acetate, in preferred embodiments, at least a portion of purified vinyl acetate stream may be recycled to reactor 100, e.g., via optional recycle line 114x, to improve diacetoxyethylene production. In one embodiment, at least 0.01 wt % of the purified vinyl acetate stream is recycled to reactor 100, e.g., at least 1 wt % or at least 5 wt %, or at least 10 wt % or even up to 20 wt %.

Figure 2:
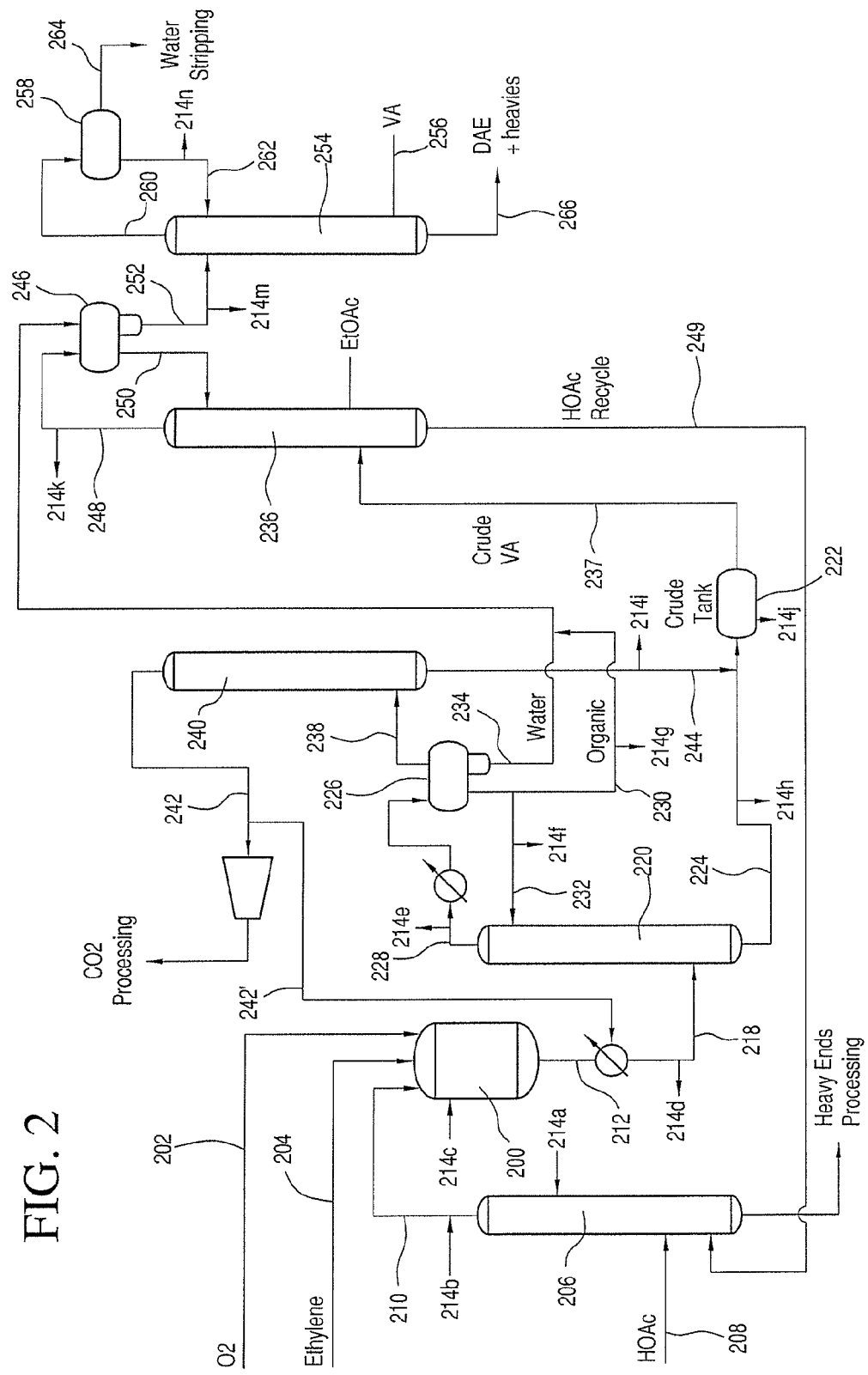
FIG. 2 is a schematic diagram of an exemplary vinyl acetate production process, which includes reaction and separation, illustrating one embodiment of the present invention.

FIG. 2 shows an exemplary vinyl acetate reaction/separation process. In FIG. 2, oxygen and ethylene are fed to reactor 200 via feed lines 202 and 204, respectively. Optionally, acetic acid is fed to vaporizer 206 via feed stream 208. Vaporized acetic acid exits vaporizer 206 and is directed to reactor 200 via line 210. In one embodiment, additional vinyl acetate is fed to vaporizer 206 via vinyl acetate feed stream 214a. In this embodiment, the vaporized acetic acid stream exiting vaporizer 206 further comprises vinyl acetate, e.g., vaporized vinyl acetate, and the vinyl acetate is fed to reactor 200 and becomes a part of the reaction mixture. In one preferred embodiment, vinyl acetate feed stream 214b is added to the vaporized acetic acid (and optionally vinyl acetate) stream in line 210. As a result, the vaporized acetic acid stream exiting vaporizer 206 further comprises vinyl acetate, e.g., vaporized vinyl acetate. The addition of vinyl acetate from stream 214a and/or 214b provides for additional vinyl acetate in the reaction mixture.

Reactor 200 reacts acetic acid, (additional) vinyl acetate, and ethylene in the presence of oxygen to form the crude vinyl acetate product, as discussed above. In one embodiment, additional vinyl acetate is fed, e.g., directly, to reactor 200 via vinyl acetate feed stream 214c. As a result, additional vinyl acetate is provided to the reaction mixture. The crude vinyl acetate stream exits reactor 200 via line 212 as an effluent stream.

The specific composition of the crude vinyl acetate composition may vary widely depending, for example, on the reaction conditions and catalyst employed. In some embodiments, the crude vinyl acetate stream may have the characteristics discussed above. Some exemplary weight percentage ranges for the crude vinyl acetate composition are presented in Table 1.

TABLE 1

Crude Vinyl Acetate Compositions

| Component | Conc. (wt. %) | Conc. (wt. %) | Conc. (wt. %) |
|---|---|---|---|
| Vinyl Acetate | 1 to 75 | 1 to 50 | 15 to 30 |
| Diacetoxyethylene | 0.1 to 1.0 | 0.15 to 1.0 | 0.15 to 0.6 |
| Acetic Acid | 1 to 80 | 1 to 50 | 5 to 25 |
| Ethylene | 10 to 90 | 10 to 50 | 20 to 40 |
| Ethane | 1 to 40 | 1 to 20 | 5 to 15 |
| Water | 1 to 20 | 1 to 10 | 2 to 8 |
| Carbon Dioxide | 1 to 75 | 1 to 50 | 2 to 35 |

Separation

As shown in FIG. 2, the vinyl acetate production system includes a separation zone 220 to recover and/or purify the vinyl acetate formed in reactor 200. Reactor effluent stream 212 is directed to the separation zone 220. In one embodiment the separation zone provides at least one derivative of reactor effluent 212. In another embodiment, the derivative stream(s) of the reactor effluent may be any stream that is yielded via the units of the separation zone 220. Preferably, the derivative streams are downstream of the reactor. Unreacted acetic acid in vapor form may be cooled and condensed. The remainder of the crude vinyl acetate composition in line 218, which is a derivative of the reactor effluent, is directed to separation zone 220. Separation zone 220 separates the contents of line 218 into a residue comprising vinyl acetate and a distillate comprising vinyl acetate, water, acetic acid, carbon monoxide, carbon dioxide, and ethyl acetate. The vinyl acetate-containing residue is directed to crude tank 222 via line 224. From crude tank 222, the vinyl acetate-containing residue may be stored and/or directed to further processing.

The separation zone effluent is optionally cooled, condensed, and directed to an overhead phase separation unit, e.g., decanter 226, via line 228, which is a derivative of the reactor effluent.

Conditions are desirably maintained in the process such that vapor contents of line 228, once cooled, condensed, and directed to decanter 226, will separate into a light phase and a heavy phase. Generally, line 228 is cooled to a temperature sufficient to condense and separate the condensable components, e.g., vinyl acetate, water, acetic acid, and other carbonyl components, into an aqueous phase and an organic phase. The organic phase exits decanter 226 via line 230. A portion of the organic phase may be refluxed back to separation zone 220, as shown by stream 232, which is a derivative of the reactor effluent. The aqueous phase exits decanter 226 and is directed via line 234 to further separation processing. As an example, line 234 may be directed to decanter 246 of an azeotrope column 236. Lines 230 and 234 optionally may be combined, as shown, and directed to decanter 246 of azeotrope column 236.

Stream 228 may include carbon monoxide, carbon dioxide, ethylene, ethane and other noncondensable gases, which may be directed via stream 238 from decanter 226 to scrubber 240. Scrubber 240 removes, inter alia, carbon monoxide, carbon dioxide, and hydrocarbons such as ethylene and ethane from stream 228. The separated noncondensable components may be conveyed to further processing, e.g., carbon dioxide removal, as shown by stream 242. In another embodiment, at least a portion of stream 242 is recycled bad to the reactor effluent or to heat exchange equipment downstream of reactor 200, as shown by stream 242'. The residue exiting scrubber 240 comprises vinyl acetate, water, and acetic acid. The residue is yielded from scrubber 240 via line 244 and may be combined with the vinyl acetate from line 224 prior to being directed to crude tank 222.

From crude tank 222, the vinyl acetate is directed to azeotrope column 236 via line 237, which is a derivative of the reactor effluent. Azeotrope column 236 separates line 237, which comprises vinyl acetate, acetic acid, and water, into a distillate stream in line 248 and a residue stream 249. Decanter 246 at the top of azeotrope column 236 receives line 234, which comprises the aqueous and organic phases from decanter 226. In addition, decanter 246 receives the distillate from azeotrope column 236. The residue from azeotrope column 236 comprises acetic acid and water. This stream may be recycled back to vaporizer 206 via line 249, or may be conveyed directly to reactor 200 (line not shown). The distillate from azeotrope column 236 comprises vinyl acetate and water and is directed to decanter 246, e.g., a reflux decanter, via line 248. Decanter 246 separates at least a portion of streams 234 and 248 into aqueous and organic phases. The organic phase, which comprises vinyl acetate, exits decanter 246 via line 252, which is a derivative of the reactor effluent, and is directed to further processing. As one example, line 252 is directed to dehydration column 254. The aqueous phase exits decanter 246 via line 250. Line 250 (or a portion thereof) may be refluxed back to azeotrope column 236.

Dehydration column 254 removes additional water from the contents of line 252, thus yielding purified vinyl acetate via line 256. The water-containing distillate of dehydration column 254 may be directed to overhead tank 258 via line 260. From overhead tank 258, line 262, which contains an amount of vinyl acetate, may be returned to dehydration column 254. Line 264, which comprises water and by-products may be directed to further processing, e.g., water stripping. The residue of dehydration column 254 exits via line 266. The residue comprises various residuals, which may be recycled or otherwise disposed.

As a result of the separation, of crude vinyl acetate stream 212, the separation zone may yield at least one vinyl acetate-containing derivative stream. These vinyl acetate-containing derivative stream(s) may be recycled to reactor 200 to promote diacetoxyethylene production therein. Some examples are discussed below.

As one example, stream 218 may contain a significant portion of vinyl acetate. Accordingly, optional vinyl acetate recycle stream 214$d$ may be withdrawn from stream 218 and recycled to reactor 200.

As another example, stream 228 may contain a significant portion of vinyl acetate and a portion of stream 228, may be withdrawn, e.g., via optional vinyl acetate recycle stream 214$e$, and recycled to reactor 200.

As another example, stream 232 may contain a significant portion of vinyl acetate and a portion of stream 232, may be withdrawn, e.g., via optional vinyl acetate recycle stream 214$f$, and recycled to reactor 200.

As another example, stream 230 may contain a significant portion of vinyl acetate and a portion of stream 230, may be withdrawn, e.g., via optional vinyl acetate recycle stream 214$g$, and recycled to reactor 200.

As another example, stream 224 may contain a significant portion of vinyl acetate and a portion of stream 224, may be withdrawn, e.g., via optional vinyl acetate recycle stream 214$h$, and recycled to reactor 200.

As another example, stream 244 may contain a significant portion of vinyl acetate and a portion of stream 244, may be withdrawn, e.g., via optional vinyl acetate recycle stream 214$i$, and recycled to reactor 200.

As another example, optional vinyl acetate recycle stream 214$j$, may be withdrawn from crude tank 222 and recycled to reactor 200.

As another example, stream 248 may contain a significant portion of vinyl acetate and a portion of stream 248, may be withdrawn, e.g., via optional vinyl acetate recycle stream 214$k$, and recycled to reactor 200.

As another example, stream 252 may contain a significant portion of vinyl acetate and a portion of stream 252, may be withdrawn, e.g., via optional vinyl acetate recycle stream 214$m$, and recycled to reactor 200.

As another example, stream 262 may contain a significant portion of vinyl acetate and a portion of stream 262, may be withdrawn, e.g., via optional vinyl acetate recycle stream 214$n$, and recycled to reactor 200.

These streams are exemplary vinyl acetate-containing derivative streams, portions of which may be recycled to reactor 200. This listing is not a complete listing and this listing is not meant to limit the scope of the invention.

In a preferred embodiment, purified vinyl acetate from line 256 is recycled to a point either upstream of the reactor, such as into acetic acid vaporizer 206, reactor feed line 210, or directly into the reactor 200 itself through lines 214$a$-$c$, respectively. Of course, additionally or alternatively, a fresh, non-recycled vinyl acetate stream can be used to feed additional vinyl acetate to reactor 200. In one embodiment, the vinyl acetate stream is provided in the vapor form. In these embodiments, if the vinyl acetate stream is in liquid form, the same may be fed to vaporizer 206 prior to reaction; if the vinyl acetate stream is in the vapor form, the same may be fed directly to reactor 200. Accordingly, if in one embodiment, a vinyl acetate-containing stream is withdrawn from the system in liquid form, it is most advantageous to recycle it into vaporizer 206 through line 214$a$.

When modified according to the present invention, enhanced levels of DAE can be separated from VAM in dehydration/distillation column 254, exiting with heavies in DAE concentrations from 4.6 wt % to 16 wt % via line 266, which DAE can be separated from other heavies by passing the effluent from line 266 into an appropriate separation unit (not shown).

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are hereby incorporated by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing a vinyl acetate composition, the process comprising the steps of:
   (a) contacting a vinyl acetate stream with acetic acid, ethylene, and oxygen to form a reaction mixture; and
   (b) reacting the reaction mixture in a reactor under conditions effective to form a crude vinyl acetate composition comprising vinyl acetate, water, acetic acid and at least 0.1 wt % diacetoxyethylenes.

2. The process of claim 1, wherein a ratio of vinyl acetate to acetic acid in the reaction mixture is at least 1:3.

3. The process of claim 1, wherein the reaction in step (b) has an ethylene conversion less than 5%.

4. The process of claim 1, further comprising the step of:
(c) separating the crude vinyl acetate composition to form a purified vinyl acetate stream comprising vinyl acetate and a by-product stream comprising diacetoxyethylene.

5. The process of claim 4, further comprising the step of:
(d) directing at least a portion of the purified vinyl acetate stream to the reactor.

6. The process of claim 1, wherein the vinyl acetate stream comprises at least a portion of a purified vinyl acetate stream.

7. The process of claim 4, wherein step (c) is performed via at least one distillation column.

8. The process of claim 1, wherein the diacetoxyethylene in the crude vinyl acetate composition comprises an isomeric mixture comprising cis-diacetoxyethylene and trans-diacetoxyethylene.

9. The process of claim 8, wherein the diacetoxyethylene in the crude vinyl acetate composition comprises at least about 0.025 wt % cis-diacetoxyethylene, and at least about 0.075 wt % trans-diacetoxyethylene.

10. The process of claim 8, wherein the ratio of cis-/trans-diacetoxyethylene in the crude vinyl acetate composition comprises from about 1:3 to about 1:1.

11. The process of claim 8, wherein the concentration of mixed diacetoxyethylenes in the crude vinyl acetate stream comprises between about 0.3 and 1 wt %.

12. The process of claim 8, wherein the concentration of mixed diacetoxyethylenes in the crude vinyl acetate stream comprises at least 0.5 wt %.

* * * * *